(12) United States Patent
Hesoun et al.

(10) Patent No.: US 7,041,834 B2
(45) Date of Patent: May 9, 2006

(54) PROCESS FOR MAKING ONDANSETRON AND INTERMEDIATES THEREOF

(75) Inventors: Dusan Hesoun, Usti nad Labem (CZ); Jiri Hykl, Praha (CZ)

(73) Assignee: Synthon IP Inc., Gainesville, VA (US)

( * ) Notice: Subject to any disclaimer, the term of this patent is extended or adjusted under 35 U.S.C. 154(b) by 0 days.

(21) Appl. No.: 10/762,552

(22) Filed: Jan. 23, 2004

(65) Prior Publication Data

US 2004/0181076 A1    Sep. 16, 2004

Related U.S. Application Data

(60) Provisional application No. 60/442,055, filed on Jan. 24, 2003.

(51) Int. Cl.
*C07D 233/61* (2006.01)
(52) U.S. Cl. ................................. 548/311.4
(58) Field of Classification Search ............... 548/311.4
See application file for complete search history.

(56) References Cited

U.S. PATENT DOCUMENTS 4,695,578 A    9/1987  Coates et al.

FOREIGN PATENT DOCUMENTS

| CN | 1105994 A | 8/1995 |
|---|---|---|
| CN | 1107474 A | 8/1995 |
| CN | 1110970 A | 11/1995 |

*Primary Examiner*—Taofiq Solola
(74) *Attorney, Agent, or Firm*—Mark R. Buscher

(57) ABSTRACT

A process useful for making ondansetron that comprises reacting a carbazolone in a reaction mixture comprising a carbazolone of formula (2), a formaldehyde or precursor thereof, and an amine of formula (3) in a non-aqueous polar solvent and in the presence of a water binding agent. The reaction product(s) can be reacted with an amine of formula (5) to form ondansetron. The water binding agent can improve the yield and/or speed of the reaction

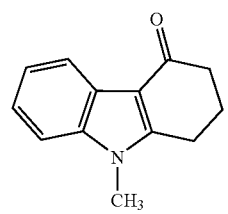

(2)

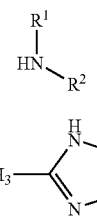

(3)

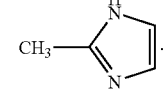

(5)

30 Claims, No Drawings

PROCESS FOR MAKING ONDANSETRON AND INTERMEDIATES THEREOF

This application claims the benefit of Provisional Application 60/442,055, filed Jan. 24, 2003, the entire contents of which are incorporated herein by reference.

BACKGROUND OF THE INVENTION

The present invention is directed to processes for making ondansetron and intermediates thereof involving a water binding agent.

Ondansetron is a pharmaceutically active agent commonly used for the treatment of nausea and vomiting, particularly when associated with cancer chemotherapy treatments. In marketed compositions (sold under brand name ZOFRAN® by Glaxo), ondansetron is used as a free base in rapidly dissolvable tablets and as a hydrochloride salt in injections, tablets for oral administration and oral solutions. Ondansetron is chemically named 1,2,3,9-tetrahydro-9-methyl-3-((2-methyl-1H-imidazol-1yl)methyl-4H-carbazol-4-one and has the following chemical structure:

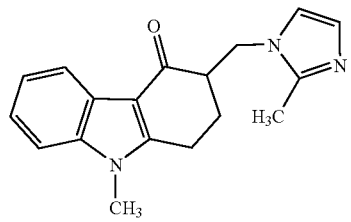

Because the ondansetron molecule has one optically active carbon, it can exist as two different enantiomers or as a mixture thereof, i.e., as a racemate. Both enantiomers are pharmaceutically active, however only the racemate is marketed thus far.

DE 3502508 and corresponding U.S. Pat. No. 4,695,578 describe ondansetron and various other 3-imidazole-tetrahydrocarbazolones, as useful in the treatment of migraine and psychotic disorders such as schizophrenia. These patents disclose several synthetic routes for making ondansetron. One example uses a transamination reaction as shown below:

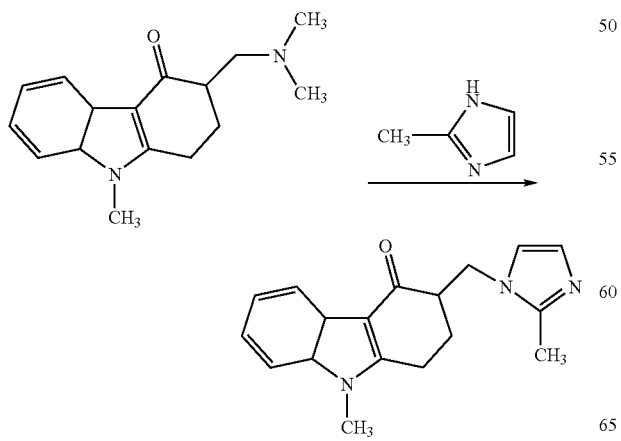

wherein an aqueous solution of 3-((dimethylamino)methyl)-1,2,3,9-tetrahydro-9-methyl-4H-carbazol-4-one hydrochloride is treated with 2-methylimidazole and heated at reflux for twenty hours. The crude ondansetron product was then recrystallized from methanol. It is not fully clear whether the transamination is a direct nucleophilic substitution or if it proceeds by an elimination-addition mechanism, i.e. via an exocyclic methylene compound, shown below, that is formed by elimination of the amine moiety.

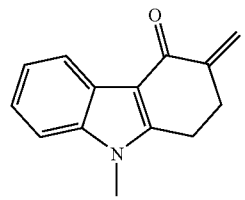

However, no example is given for making the 3-dimethylamino-9-methyl-carbazolone starting material used therein. The synthesis of an analogous 3-dimethylamino-9-phenyl-carbazolone is shown as the only example given of how to make a 3-dimethylamino substituted starting compound. In this example, a solution of 1,2,3,9-tetrahydro-9-phenyl-4Hcarbazol-4-one, dimethylamine hydrochloride and paraformaldehyde are stirred in glacial acetic acid under reflux for forty-two (42) hours and then allowed to cool. After concentrating in vacuo, a residual brown gum was stirred with water, ethyl acetate and brine. The resulting solid was filtered off, washed and dried.

Chinese patents CN 1107474 and CN 1110970 describe the synthesis of ondansetron by reacting an N-methyltetrahydrocarbazol-4-one with paraformaldehyde, 2-methylimidazole and dimethylamine or diethylamine hydrochloride in acetic acid. Reaction times are 20–30 hours and the reported yields are rather poor.

CN 1105994 describes the same reaction, however performed in inert solvent under presence of acidic ion-exchange resin. The reaction temperatures are 50–140° C. and reaction times are 80–200 hours.

While the formation of ondansetron by a transamination reaction with 2-methylimidazole is known, it would be desirable to improve the reaction time and/or yield, especially for commercial scale production of ondansetron.

SUMMARY OF THE INVENTION

The present invention relates to process for making ondansetron or its intermediates that uses a water binding agent. Accordingly, a first aspect of the present invention relates to a process which comprises contacting a carbazolone of formula (2),

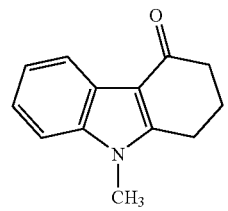

(2)

formaldehyde or a formaldehyde precursor, and an amine of formula (3) or a salt thereof

(3)

wherein $R^1$ and $R^2$ each independently represent a $C_1$ to $C_4$ alkyl group or together with the nitrogen atom they form a 5- or 6-membered ring, in a non-aqueous polar solvent and in the presence of a water binding agent to form a reaction mixture; and reacting the carbazolone of formula (2) in the reaction mixture to form an intermediate-carbazolone reaction mixture. The water binding agent, which is hereinafter defined, is preferably acetic anhydride or phosphorus pentoxide anhydrate. The reaction can be carried out in a relatively short time such as less than 3 hours and is preferably carried out such that not more than 10% of the carbazolone remains after two hours, more preferably after one hour, from the start of the reaction. After the intermediate-carbazolone reaction mixture is formed, an imidazole of formula (5) or a salt thereof,

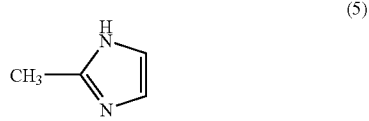
(5)

can be reacted in the reaction mixture to form a compound of formula (1), i.e. ondansetron.

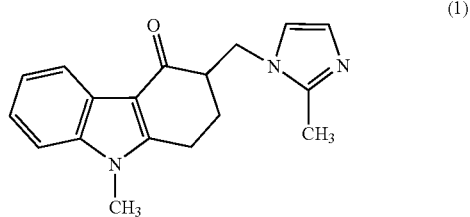
(1)

Another aspect of the present invention relates to a process for making ondansetron, which comprises the following steps:

(a) combining in a non-aqueous polar solvent a carbazolone of formula (2);

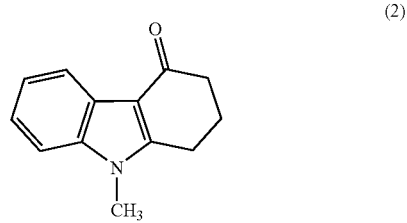
(2)

paraformaldehyde; an amine of formula (3);

(3)

wherein $R^1$ and $R^2$ each independently represent a $C_1$ to $C_4$ alkyl group or together with the nitrogen atom they form a 5- or 6-membered ring; a water binding agent; and an organic acid to form a reaction mixture;

(b) reacting said reaction mixture at a temperature from 50° C. to 150° C. until at least 50% of said carbazolone is converted to a reaction product; and (c) subsequently reacting an imidazole of formula (5) in said reaction product-containing reaction mixture

(5)

or a salt thereof, to form ondansetron. The reaction step (b) is preferably carried out in 1 hour or less and step (c) is preferably carried out in 6 hours or less.

DETAILED DESCRIPTION OF THE INVENTION

The present invention is based on the discovery that the conversion of a carbazolone of formula (2) to ondansetron of formula (1) can be carried out more easily, and typically more rapidly, than the above-described known processes. The improvements are believed to be due to the presence of a water binding agent during at least the reaction of the carbazolone of formula (2). A "water binding agent" as used herein means a substance that is capable of binding or taking up water during the reaction in order to render the water unavailable for any reverse or equilibrium reaction. Preferably the water binding agent chemically bonds (covalently bonds) the water molecule; that is, the water binding agent reacts with water to form a new chemical compound. Typically water binding agents are organic or inorganic acids such as acetic anhydride, phosphorous pentoxide anhydrate, or methane sulfonic acid. It should be noted that acetic anhydride and phosphorous pentoxide anhydrate chemically react with water and are thus examples of the chemically bonding type of water binding agent. Methane sulfonic acid, in contrast, coordinates the water molecules and is not a chemically bonding type, albeit it is a water binding agent. Other water binding agents include water binding polymers and resins such as DOWEX®(Dow Chemical) as well as other materials known in the art. Typically the water binding agent is a non-polymeric water binding agent. The most preferred water binding agent is acetic anhydride, also known as acetic oxide, and can be expressed as the molecular formula $(CH_3CO)_2O$. Generally the water binding agent is present in an amount sufficient to remove at least about a stoichiometric amount of water relative to the carbazolone of formula (2). Typically 0.5 to 2 equivalents, preferably 1 to 1.5 equivalents per 1 mole of the carbazolone of formula (2). For acetic anhydride, preferably about 1 to 1.5, especially 1.1 to 1.3 moles are provided per each mole of the carbazolone of formula (2).

The carbazolone of formula (2) is reacted in an apparent condensation reaction, a so-called Mannich reaction, with formaldehyde or a formaldehyde precursor and an amine of formula (3) or a salt thereof. It is believed that this reaction produces an amine carbazolone for formula (4)

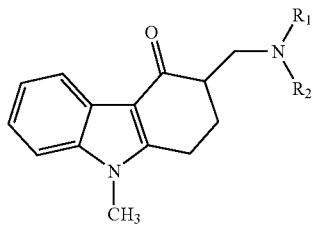

(4)

wherein $R^1$ and $R^2$ have the same meaning as in formula (3). The reaction, which generally proceeds under acidic conditions, produces water as a side product. The presence of a water binding agent in the present invention can bind this water and thus theoretically shift the reaction equilibrium to the product side. The amine carbazolone of formula (4) is reacted with an imidazole of formula (5) in what is believed to be a transamination reaction to form ondansetron of formula (1). However, it is not fully clear whether the transamination is a direct nucleophilic substitution or if it proceeds by an elimination-addition mechanism, i.e. via an exocyclic methylene compound (6)

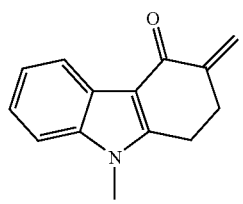

(6)

that is formed by elimination of the amine moiety from the compound (4). The formation of the exocyclic methylene compound (6) has been observed during the Mannich reaction. It could also be formed as a product of degradation of ondansetron. Thus, the variants of the process for making ondansetron (1) from the carbazolone (2) may be depicted as shown in the following scheme.

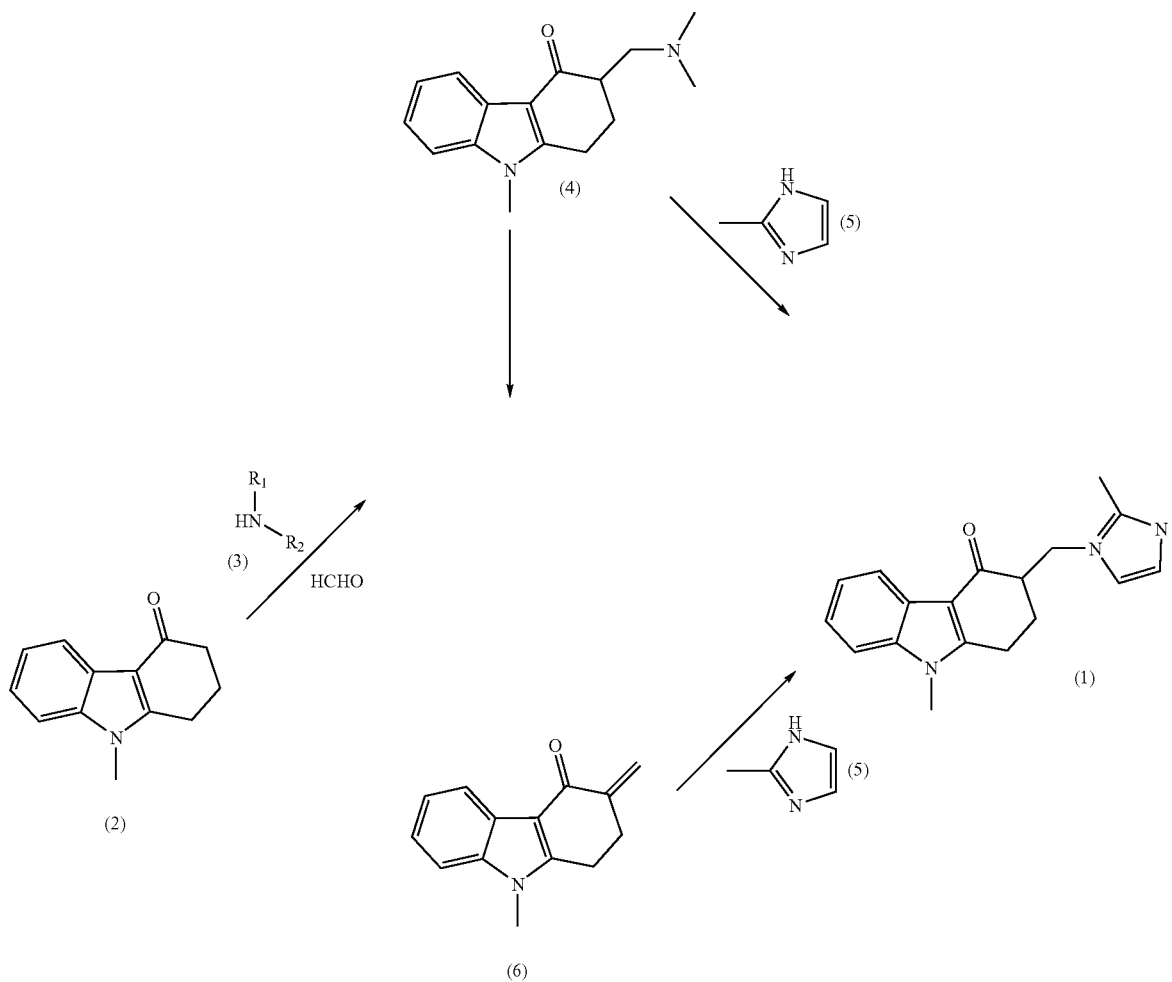

In the present invention, a carbazolone of formula (2), a formaldehyde or formaldehyde precursor, an amine of formula (3) or a salt thereof and a water binding agent are combined in a non-aqueous polar solvent to form a reaction mixture.

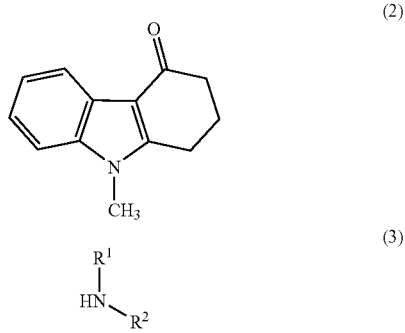

$R^1$ and $R^2$ of formula (3) each independently represent a $C_1$ to $C_4$ alkyl group, preferably methyl or ethyl, or together with the nitrogen atom they form a 5- or 6-membered ring, preferably a nitrogen-containing ring such as piperidine, pyrrolidine, and morpholine. Preferably $R^1$ and $R^2$ are the same and more preferably are methyl or ethyl. The salts of the amine of formula (3) are typically acid addition salts wherein the acid is an organic or inorganic acid and is conveniently hydrochloric acid, i.e. the hydrochloride salts are preferred. The preferred amines of formula (3) are dimethylamine, diethylamine, piperidine, morpholine, and the hydrochloride salts thereof. The formaldehyde precursor includes any compound that forms formaldehyde in situ, e.g. under the reaction conditions employed. Preferably, the formaldehyde precursor is paraformaldehyde, also known as polyoxymethylene, which upon heating de-polymerizes into formaldehyde. Paraformaldehyde, being non-gaseous, is generally easier to handle than formaldehyde per se and has been commonly used in the above-described prior patent literature.

The non-aqueous polar solvent includes any solvent suitable for facilitating the formation of the reaction mixture. Generally all of the reactants are soluble in, and are dissolved in, the solvent. The water binding agent need not be dissolved in the solvent but is only required to be in reactive contact therewith, i.e. as a suspension of solid material in the reaction mixture or as a column upon which the reaction mixture is run through, etc. Typically the reaction mixture is a single phase solution. Suitable solvents include an amide, a ketone, an ester, an acid or a mixture thereof. Preferably, the solvent is dimethylformamide.

The reaction mixture preferably additionally contains an organic acid such as an aliphatic acid. Generally the aliphatic acid contains 2 to 12 carbon atoms and is preferably acetic acid.

The molar ratios of the carbazolone of formula (2), amine of formula (3), and formaldehyde or precursor thereof, provided in the reaction mixture are not particularly limited. For economy, the amine of formula (3) and the formaldehyde, optionally as a precursor thereof, are generally provided in equivalent or molar excessive amounts, i.e., 1–1.5 moles, typically 1.1 to 1.3 moles, per mole of the carbazolone of formula (2). For clarity, the amount of paraformaldehyde would be calculated based on the amount of formaldehyde it would provide. The amount of acid provided in the reaction mixture is generally small and typically within the range of 0.01 to 0.3 moles, preferably 0.05–0.15 moles, per each mole of the carbazolone of formula (2).

After the reaction mixture is formed, the carbazolone of formula (2) is reacted in the reaction mixture such that the carbazolone of formula (2) is consumed and/or converted to an intermediate, thereby forming an intermediate-carbazolone reaction mixture. The intermediate is believed to be an amine-carbazolone of formula (4) and/or the exocyclic methylene compound of formula (6) as discussed above. Whatever the reaction product, the intermediate-carbazolone reaction mixture is formed as soon as the carbazolone begins to react; i.e., the amount of carbazolone of formula (2) begins to decrease. The content and relative proportions of ingredients in the intermediate-carbazolone reaction mixture will generally change over time as more and more of the carbazolone of formula (2) is reacted and hence converted into product. Thus, whether 1% or 100%, and everywhere in between, of the carbazolone of formula (2) has been reacted, the corresponding mixtures are all intermediate-carbazolone reaction mixtures. It is also possible that the initial reaction product in the intermediate-carbazolone reaction mixture is subsequently reacted or transformed such as from an amine-carbazolone of formula (4) to the exocyclic methylene compound of formula (6). If this particular conversion is being carried out in the intermediate-carbazolone reaction mixture, then it may be possible to use less of the amine of formula (3) in the reaction mixture as the amine is liberated in the conversion to the exocyclic methylene compound of formula (6). Therefore, small amounts of the amine could be used, such as 0.2 moles or more, including 0.5 moles or more, per each mole of the carbazolone. But such a sub-stoichiometric amount is generally not preferred as it is believed to result in slower conversion rates.

The reaction generally proceeds under acidic conditions and typically at an elevated temperature in the range of 50° C. to 150° C., preferably 90° C. to 120° C., and in some embodiments 100° C. to 110° C.

This reaction can advantageously proceed at a relatively rapid pace. Typically the carbazolone of formula (2) is exhausted and/or no further reaction thereof occurs within three hours. Generally, 10% or less of the carbazolone of formula (2) remains after 2 hours, more preferably after 1 hour, from the start of the reacting step. The reaction product(s), such as the amine-carbazolone of formula (4), can be isolated from the reaction mixture before being subsequently converted to ondansetron. Preferably, however, the process continues without isolation of any reaction product.

The imidazole of formula (5)

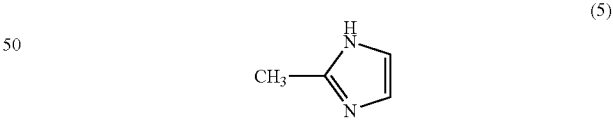

is subsequently reacted in the intermediate-carbazolone reaction mixture to form ondansetron of formula (1).

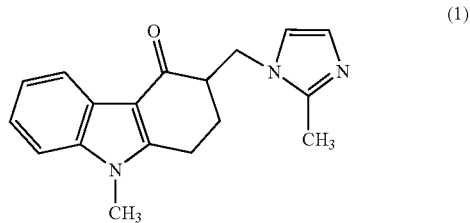

The imidazole of formula (5) can form ondansetron with any suitable reaction partner formed in the intermediate-carbazolone reaction mixture by the consumption of the carbazolone of formula (2); e.g. the amine-carbazolone of formula (4) or the exocyclic methylene of formula (6). The imidazole of formula (5) can be added to the reaction mixture before, during, or after the reaction of the carbazolone of formula (2) begins. Typically the imidazole of formula (5) is added to the reaction mixture after the carbazolone reaction has begun, generally within 0.5 to 2 hours, more preferably 0.5 to 1.5 hours, after the start of the carbazolone reaction. Alternatively, the addition of the imidazole of formula (5) to the reaction mixture typically is carried out after said carbazolone reaction has substantially begun, preferably at least 50% of the carbazolone has been reacted, more typically at least 80%, and preferably after said carbazolone reaction is substantially complete, i.e. the residual amount of carbazolone, if any, is essentially stable. The reaction of the imidazole of formula (5) preferably begins as soon as it is contacted with the reaction mixture; i.e. the conditions are amenable to the imidazole reaction. In this regard, the imidazole reaction does not require a catalyst, although one, e.g. iodine or alumina, can be provided if desired. The reaction temperature is typically from 90° C. to 120° C.

The duration of the reaction of the imidazole of formula (5) is also preferably relatively rapid, frequently taking eight hours or less, preferably 6 hours or less, more preferably 5 hours or less, from when the imidazole reaction begins. The reaction duration refers to the amount of time spent carrying out the reaction and not necessarily the time spent in the reaction vessel. For example, if the imidazole is completely reacted, or reaches an equilibrium where essentially no further yield is achieved, then the imidazole reaction is complete, regardless of whether the reaction mixture and/or ondansetron is removed from the vessel at that point. The completeness of the imidazole (or the carbazolone) reaction can be monitored by any suitable means or techniques such as HPLC, if desired.

In a preferred embodiment, the formation of the reaction mixture, the carbazolone reaction and the imidazole reaction occur in the same vessel as a so called one pot process. Furthermore, the carbazolone reaction is first conducted and substantially completed before said imidazole of formula (5) is contacted with the reaction mixture and reacted therein to form ondansetron. Preferably, the carbazolone reaction is complete within 1 hour and the imidazole reaction is complete within 5 hours. In this way the overall conversion of the carbazolone of formula (2) to ondansetron can be accomplished in less than eight hours, preferably in about 6 hours or less, even on industrial or kilogram scale production; i.e., at least one kilogram, preferably at least 5 kg, more preferably at least 10 kg including 50 kg and 100 kg or more yields of ondansetron.

As indicated above, it is believed that the presence of a water binding agent, such as acetic anhydride, is responsible for improving the speed and/or yield of the inventive process. For example, studies have shown that to achieve 90% conversion of the carbazolone in acetic acid at reflux temperatures takes 3 or more hours, while at 80° C. it takes at least 7 hours. In contrast, when the reaction is carried out in the presence of acetic anhydride, the 90% conversion can take less than 1 hour. Further, the subsequent imidazole reaction is also performed more rapidly such that the entire process can be of a fast nature with high yield.

The produced ondansetron may be isolated from the reaction mixture by diluting the reaction mixture with water and adjusting the pH, if necessary, to a value of 7–9, preferably to about 8. The product separates in solid state, as a free base, and is collected by an ordinary separation method(s) such as filtration or centrifugation. Isolated crude ondansetron base may contain some impurities and may be purified into the desired degree of purity by several methods. If desired the ondansetron free base can be converted to an acid addition salt, especially a pharmaceutically acceptable acid addition salt such as ondansetron hydrochloride.

All of the starting materials used in the process of the present invention are commercially available and/or readily obtainable by methods and techniques well known in the art. The following non-limiting example is provided to illustrate the present invention.

EXAMPLE a) Charge, under stirring, the reactor with 6.4 l of dimethylformamide, 32 ml of acetic acid, 0.8 l of acetic anhydride, 0.8 kg of dimethylamine hydrochloride, 290 g of paraformaldehyde and 1.6 kg of carbazolone (2). Heat the mixture to 100–110° C. and stir for 1 hour. Add 4.0 kg of 2-methyl-1H-imidazole under stirring and stir the mixture for 5 hours. Cool to 80–100° C., dilute the reaction mixture with 50 l of water and allow to cool to ambient temperature. Control the pH to higher than 8 and filter the precipitated solid. Wash the solid twice with 3.2 l of water and dry.

b) Charge the reactor with 2.1 kg of the product prepared in preceded step, 115 l of methanol and 0.21 kg of activated charcoal. Heat under stirring to reflux and maintain the reflux for 1 hour. Filter through pressure filter to a clean reactor, wash the filter cake with 2×10 l of hot methanol. Distill off about 100 l of methanol from the combined solution. Under stirring, cool slowly the distillation rest to 0–5° C. and stir at this temperature for 1 hour. Filter the resulted precipitate, wash it with 2×3.2 l of cold methanol and dry.

Yield: 1.6 kg.

Each of the patents mentioned above are incorporated herein by reference in their entirety. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

What is claimed is:

1. A process, which comprises contacting a carbazolone of formula (2),

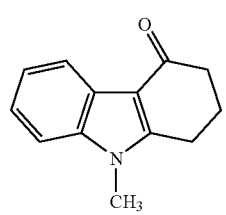

(2)

formaldehyde or a formaldehyde precursor, and an amine of formula (3) or a salt thereof

wherein R¹ and R² each independently represent a $C_1$ to $C_4$ alkyl group or together with the nitrogen atom they form a 5- or 6-membered ring, in a non-aqueous polar solvent and in the presence of a non-polymeric water binding agent to form a reaction mixture;
reacting said carbazolone of formula (2) in said reaction mixture to form an intermediate-carbazolone reaction mixture; and
reacting in said intermediate-carbazolone reaction mixture an imidazole of formula (5)

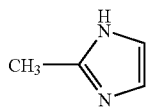

or a salt thereof to form a compound of formula (1)

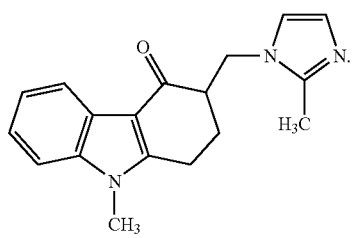

2. The process according to claim 1, wherein said formaldehyde precursor is paraformaldehyde.

3. The process according to claim 1, wherein said amine of formula (3) is selected from the group consisting of dimethylamine, diethylamine, piperidine, morpholine and the hydrochloride salts thereof.

4. The process according to claim 3, wherein said amine of formula (3) is dimethylamine hydrochloride.

5. The process according to claim 1, which further comprises providing an organic acid in said reaction mixture.

6. The process according to claim 5, wherein said organic acid is acetic acid.

7. The process according to claim 1, wherein said solvent is dimethylformamide.

8. The process according to claim 1, wherein said water binding agent chemically bonds with water.

9. The process according to claim 1, wherein said water binding agent is acetic anhydride, methane sulfonic acid or phosphorus pentoxide anhydrate.

10. The process according to claim 9, wherein said water binding agent is acetic anhydride.

11. The process according to claim 1, wherein not more than 10% a of said carbazolone of formula (2) remains after two hours of reacting.

12. The process according to claim 10, wherein not more than 10% of said carbazolone of formula (2) remains after one hour of reacting.

13. The process according to claim 1, wherein said carbazolone reacting step is carried out at a temperature within the range of 50° C. to 150° C.

14. The process according to claim 1, wherein said imidazole compound of formula (5) is the hydrochloride salt thereof.

15. The process according to claim 1, wherein said imidazole compound is provided in said reaction mixture substantially simultaneously with the formation of said reaction mixture.

16. The process according to claim 1, wherein said imidazole compound is contacted with said intermediate-carbazolone reaction mixture 0.5 to 2 hours after said reacting of said carbazolone of formula (2) begins.

17. The process according to claim 16, wherein said imidazole compound is contacted with said intermediate-carbazolone reaction mixture after said reacting of said carbazolone of formula (2) is substantially complete.

18. The process according to claim 17, wherein said imidazole compound is contacted with said intermediate-carbazolone reaction mixture 0.5 to 1.5 hours after said reacting of said carbazolone of formula (2) begins.

19. The process according to claim 1, wherein said reaction of said imidazole compound of formula (5) is substantially complete within 8 hours from when it begins.

20. The process according to claim 19, wherein said reaction of said imidazole compound of formula (5) is substantially complete within 5 hours from when it begins.

21. The process according to claim 1, wherein said reaction, of said imidazole compound of formula (5) is carried out substantially simultaneously with said reaction of said carbazolone of formula (2).

22. The process according to claim 1, wherein said reaction of said imidazole compound of formula (5) is carried out after said reaction of said carbazolone of formula (2) is substantially complete.

23. The process according to claim 1, wherein the total reaction time of said reaction of said carbazolone of formula (2) and said reaction of said imidazole of formula (5) is not more than 8 hours.

24. The process according to claim 23, wherein said total reaction time is not more than 7 hours.

25. The process according to claim 24, wherein said total reaction time is not more than 6 hours.

26. The process according to claim 1, wherein said reaction of said imidazole compound of formula (5) is carried out at one or more temperatures in the range of 90° C. to 120° C.

27. The process according to claim 1, which further comprises converting said compound of formula (1) to a pharmaceutically acceptable salt thereof.

28. A process for making ondansetron, which comprises the following steps:
(a) combining in a non-aqueous polar solvent a carbazolone of formula (2);

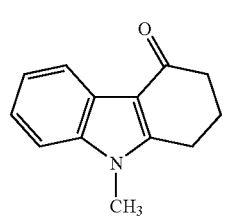

paraformaldehyde; an amine of formula (3) or a salt thereof;

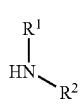
(3)

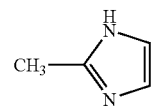
(5)

wherein $R^1$ and $R^2$ each independently represent a $C_1$ to $C_4$ alkyl group or together with the nitrogen atom they form a 5- or 6-membered ring; a water binding agent; and an organic acid to form a reaction mixture;

(b) reacting said reaction mixture at a temperature from 50° C. to 150° C. until at least 50% of said carbazolone is converted to a reaction product; and (c) subsequently reacting an imidazole of formula (5) in said reaction product-containing reaction mixture or a salt thereof, to form ondansetron.

29. The process according to claim 28, wherein said reacting step (b) is carried out for not more than 1 hour and said reacting step (c) is carried out for not more than 5 hours.

30. The process according to claim 29, wherein said non-aqueous polar solvent is dimethylformamide, said water binding agent is acetic anhydride, and said organic acid is acetic acid.

* * * * *